(12) United States Patent
Robert et al.

(10) Patent No.: US 11,253,004 B2
(45) Date of Patent: Feb. 22, 2022

(54) POWER MANAGEMENT METHOD AND SYSTEM FOR A BATTERY POWERED AEROSOL-GENERATING DEVICE

(71) Applicant: Philip Morris Products S.A., Neuchatel (CH)

(72) Inventors: Jacques Robert, Le Mont-sur-Lausanne (CH); Michel Bessant, Neuchatel (CH); Riccardo Riva Reggiori, St-Sulpice (CH)

(73) Assignee: Philip Morris Products S.A., Neuchatel (CH)

( * ) Notice: Subject to any disclaimer, the term of this patent is extended or adjusted under 35 U.S.C. 154(b) by 341 days.

(21) Appl. No.: 16/491,932

(22) PCT Filed: Mar. 9, 2018

(86) PCT No.: PCT/EP2018/055966
§ 371 (c)(1),
(2) Date: Sep. 6, 2019

(87) PCT Pub. No.: WO2018/166925
PCT Pub. Date: Sep. 20, 2018

(65) Prior Publication Data
US 2020/0037668 A1     Feb. 6, 2020

(30) Foreign Application Priority Data

Mar. 14, 2017  (EP) .................................... 17160953

(51) Int. Cl.
*A24F 40/50* (2020.01)
*A24B 15/167* (2020.01)
(Continued)

(52) U.S. Cl.
CPC ............ *A24F 40/50* (2020.01); *A24B 15/167* (2016.11); *A61M 15/06* (2013.01); *A24F 40/20* (2020.01);
(Continued)

(58) Field of Classification Search
CPC ................. A24F 40/50; A24F 15/167; A61M 2205/3317
(Continued)

(56) References Cited

U.S. PATENT DOCUMENTS 8,393,331 B2 * 3/2013 Hon ...................... A61M 11/044
131/194
8,499,766 B1 * 8/2013 Newton .................. A24F 40/40
131/273
(Continued)

FOREIGN PATENT DOCUMENTS

CN    104881063 A    9/2015
CN    105792688 A    7/2016
(Continued)

OTHER PUBLICATIONS

Notice of Allowance dated Aug. 16, 2021 in Russian Patent Application No. 2019130860 (with English translation), 16 pages.
(Continued)

*Primary Examiner* — Alexander Gilman
(74) *Attorney, Agent, or Firm* — Oblon, McClelland, Maier & Neustadt, L.L.P.

(57) ABSTRACT

A method for controlling power supplied to an aerosol-generating element of an aerosol-generating device is provided, the aerosol-generating device including an aerosol-generating element, a control unit, and a battery configured to deliver power to the aerosol-generating element and to the control unit, the control unit being configured to adjust a duty cycle of a current supplied from the battery to the
(Continued)

aerosol-generating element; and the method including measuring, using a measuring unit, at least one first characteristic of the battery, the at least one first characteristic comprising a temperature of the battery; and adjusting, using the control unit, a value of the duty cycle based on a predetermined rule which outputs the value of duty cycle based on the measured at least one battery characteristic. An aerosol-generating device is also provided.

15 Claims, 5 Drawing Sheets

(51) Int. Cl.
*A61M 15/06* (2006.01)
*A24F 40/20* (2020.01)

(52) U.S. Cl.
CPC .............. *A61M 2205/3317* (2013.01); *A61M 2205/8206* (2013.01); *A61M 2205/8237* (2013.01); *H01M 2220/30* (2013.01)

(58) Field of Classification Search
USPC .......................................................... 131/329
See application file for complete search history.

(56) References Cited

U.S. PATENT DOCUMENTS

| | | | |
|---|---|---|---|
| 9,949,507 B2 * | 4/2018 | Flick | A24F 40/50 |
| 10,439,419 B2 * | 10/2019 | Bernauer | H01M 10/42 |
| 10,645,971 B2 * | 5/2020 | Zitzke | H05B 1/0244 |
| 10,687,557 B2 * | 6/2020 | Tucker | H05B 3/46 |
| 10,777,091 B2 * | 9/2020 | Pandolfino | A24F 40/50 |
| 10,842,197 B2 * | 11/2020 | Bless | A24F 40/42 |
| 10,912,335 B2 * | 2/2021 | Zitzke | A24F 40/42 |
| 10,966,460 B2 * | 4/2021 | Frisbee | H05B 1/0202 |
| 10,986,875 B2 * | 4/2021 | Fisher | H02J 7/0029 |
| 11,071,327 B2 * | 7/2021 | Jain | A24F 40/51 |
| 11,103,012 B2 * | 8/2021 | Sur | B65D 83/72 |
| 2015/0128967 A1 | 5/2015 | Robinson et al. | |
| 2016/0213066 A1 * | 7/2016 | Zitzke | A61M 11/042 |
| 2016/0219933 A1 * | 8/2016 | Henry, Jr | A24F 40/65 |
| 2016/0242466 A1 * | 8/2016 | Lord | G06F 1/3296 |
| 2016/0262453 A1 * | 9/2016 | Ampolini | A24F 40/40 |
| 2016/0309788 A1 * | 10/2016 | Hawes | A24F 40/53 |
| 2016/0324216 A1 * | 11/2016 | Li | A24F 40/46 |
| 2016/0331037 A1 * | 11/2016 | Cameron | A24F 40/46 |
| 2016/0366947 A1 * | 12/2016 | Monsees | A24F 40/42 |
| 2017/0000192 A1 * | 1/2017 | Li | G06K 9/03 |
| 2017/0013880 A1 * | 1/2017 | O'Brien | A61M 11/042 |
| 2017/0020191 A1 * | 1/2017 | Lamb | A61M 11/042 |
| 2017/0027234 A1 * | 2/2017 | Farine | A24F 40/53 |
| 2017/0079323 A1 * | 3/2017 | Wang | H01M 50/20 |
| 2017/0112191 A1 * | 4/2017 | Sur | A61M 11/042 |
| 2017/0150757 A1 * | 6/2017 | Worm | A24F 15/01 |
| 2017/0174914 A1 * | 6/2017 | Matsumura | H01L 21/288 |
| 2017/0207499 A1 * | 7/2017 | Leadley | H01M 10/425 |
| 2017/0325502 A1 * | 11/2017 | Nelson | A24F 40/70 |
| 2017/0036741 A1 | 12/2017 | Hon | |
| 2017/0367410 A1 * | 12/2017 | Hon | A24F 40/50 |
| 2018/0007966 A1 * | 1/2018 | Li | A24F 40/42 |
| 2018/0027879 A1 * | 2/2018 | Gavrielov | A24F 40/70 |
| 2018/0132530 A1 * | 5/2018 | Rogers | A24F 40/40 |
| 2019/0014819 A1 * | 1/2019 | Sur | B05B 17/0646 |
| 2019/0133187 A1 * | 5/2019 | Spencer | A24D 1/20 |
| 2019/0281892 A1 * | 9/2019 | Hejazi | A24F 40/44 |
| 2019/0380389 A1 * | 12/2019 | Hong | A24F 40/65 |
| 2020/0120991 A1 * | 4/2020 | Hatton | A61M 15/06 |
| 2020/0154771 A1 * | 5/2020 | Otiaba | A24F 40/51 |

FOREIGN PATENT DOCUMENTS

| | | |
|---|---|---|
| DE | 20 2013 010 986 U1 | 2/2014 |
| EP | 2 856 893 A1 | 4/2015 |
| GB | 2528711 A | 2/2016 |
| GB | 2533651 A | 6/2016 |
| KR | 10-2016-0016552 A | 2/2016 |
| RU | 2 600 915 C1 | 10/2016 |
| WO | WO 2014/029880 A2 | 2/2014 |

OTHER PUBLICATIONS

Extended European Search Report dated Sep. 18, 2017, in Patent Application No. 17160953.0, 9 pages.
International Search Report and Written Opinion dated Jul. 13, 2018 in PCT/EP2018/055966 filed Mar. 9, 2018.
Chinese Office Action dated Dec. 13, 2021 in corresponding Chinese Patent Application No. 201880015974.3 (with English translation), 9 pages.

* cited by examiner

POWER MANAGEMENT METHOD AND SYSTEM FOR A BATTERY POWERED AEROSOL-GENERATING DEVICE

The invention relates to battery powered aerosol-generating devices, and in particular to a method and system for controlling the supply of power to an aerosol-generating element that improves the reliability of the device under different operating conditions.

Typically, a battery powered aerosol-generating device, comprises an aerosol-generating element, such as a resistive heating element, that is connected to a battery.

When an aerosol-generating device is first activated it is desirable to minimise the time taken for the device to deliver aerosol. Particularly for devices generating aerosol for inhalation, if the time taken to deliver a first puff is too long then users will become frustrated. In a device that uses a resistive heater, this means increasing the temperature of the heater as quickly as possible.

However, there are potential difficulties with simply delivering maximum power to the aerosol-generating element at the outset. Aerosol-generating devices typically comprise a microcontroller unit (MCU) and various electronic components that need a minimum voltage to operate correctly. Below this voltage, correct operation cannot be guaranteed. This is especially true for MCUs. But delivering maximum power from the battery, especially when the battery is cold, can lead to insufficient voltage at the MCU.

It is well known that drawing a high current from a battery reduces its output voltage. This is due to the internal resistance of the battery. It is also known that at low temperature, the internal resistance of a battery is higher, thereby limiting the maximum discharge current. In addition, the output voltage of a battery is lower at low temperature for any given output battery current. And in those cases in which the aerosol-generating element is a resistive heater with a positive temperature coefficient, the resistance of the heater will be at its lowest prior to activation and will increase with the temperature, leading to a greater voltage dropped across the internal resistance of the battery.

For these reasons, it is possible that applying maximum power at the outset may cause the device to stop operating because the output voltage from the battery drops below a minimum voltage required for the MCU.

It would be desirable to be able to extract the maximum power from the battery to make the device fully operational within the shortest amount of time, while ensuring that the output battery voltage is maintained above a minimum threshold voltage that ensures a correct operation of the MCU.

To regulate the operation of the aerosol-generating device, the battery can be dynamically connected to the aerosol-generating element so that a duty cycle of the current and voltage applied to the aerosol-generating element can be varied.

In a first aspect, there is provided a method for controlling power supplied to an aerosol-generating element of an aerosol-generating device, the aerosol-generating device comprising an aerosol-generating element, a control unit, and a battery for delivering power to the aerosol-generating element and to the control unit, the control unit configured to adjust a duty cycle of a current supplied from the battery to the aerosol-generating element, wherein the method comprises the steps of:

measuring using a measuring unit, at least one first characteristic of the battery; and adjusting, using the control unit, a value of the duty cycle based on a predetermined rule which outputs a value of duty cycle based on the measured at least one battery characteristic.

By controlling the duty cycle of the current supplied from the battery in this way, as high a duty cycle as possible can be used while maintaining the voltage at the control unit at or above a minimum operating voltage. The predetermined rule may be chosen to ensure that the voltage at the control unit exceeds a threshold voltage.

The at least one battery first characteristic may comprise a temperature of the battery. The output voltage of a battery is affected by temperature because its internal resistance is affected by temperature. A thermistor or other dedicated temperature sensor may be used to obtain a measure of the temperature of the battery. Alternatively, the at least one battery characteristic may comprise a measure of battery age, such a count of charge and discharge cycles that the battery has completed. A count of charge and discharge cycles may be recorded and stored in an memory within the aerosol-generating device. Alternatively, the at least one battery characteristic may comprise an internal resistance of the battery or an impedance of the battery. The internal resistance of the battery may be measured using well known techniques, such as the method described in WO2014/029880, Battery impedance measurement may be done by injecting a small AC current into the battery and measuring the associated AC voltage.

Advantageously, the steps of measuring and adjusting are carried out periodically. As the battery discharges it will dissipate some heat as a result of its internal resistance. This may result in a reduced internal resistance. The duty cycle may be adjusted periodically, for example every 0.5 seconds, to account for the reducing internal resistance of the battery. In this way, the duty cycle may start at a low level and may be progressively increased while ensuring that the control unit receives sufficient voltage.

Advantageously, the predetermined rule defines a plurality of intervals of values related to the at least one characteristic of the battery, each interval being associated with a respective duty cycle value, the step of adjusting a value of the duty cycle comprising outputting the duty cycle value associated with an interval that includes a value of the measured at least one battery characteristic. The intervals of values related to the at least one characteristic of the battery may be sequential. The intervals of values related to the at least one characteristic of the battery may be non-overlapping.

For example, in one embodiment, the at least one characteristic of the battery is temperature and the predetermined rule comprises the following intervals and associated duty cycle values:

1/If the battery temperature is between −10° C. and −5° C., use a duty cycle value of 10%.

2/If the battery temperature is between −5° C. and 0° C., use a duty cycle value of 20%.

3/If the battery temperature is between 0° C. and 5° C., use a duty cycle value of 30%.

4/If the battery temperature is between 5° C. and 10° C., use a duty cycle value of 40%.

5/If the battery temperature is between 10° C. and 15° C., use a duty cycle value of 50%.

6/If the battery temperature is between 15° C. and 20° C., use a duty cycle value of 60%.

7/If the battery temperature is above 20° C., use any desired duty cycle.

With a handheld device it may be expected for the battery temperature to rise during use, because of heat generated internally in the battery and heat generated by one or more heaters in the device, and from the user holding the device and transferring body heat to the battery.

The method may further comprise a step of measuring at least one second characteristic of the aerosol-generating device and selecting the value of a duty cycle based on a predetermined sub-rule and on the measured value of at least one second characteristic of the aerosol-generating device, wherein the predetermined sub-rule is selected from a group of predetermined sub-rules based on the measured at least one first characteristic of the battery.

The steps of measuring at least one second characteristic and selecting the value of duty cycle are carried out periodically. The duty cycle may be adjusted periodically, for example every 0.5 seconds, to account for a changing value of the second characteristic of the aerosol-generating element. In this way, the duty cycle may start at a low level and may be progressively increased while ensuring that the control unit receives sufficient voltage.

The at least one second characteristic of the aerosol-generating device may comprise an electrical resistance of the aerosol-generating element. An electrical resistance of the aerosol-generating element may change during use, as it may be temperature dependent. The aerosol-generating element may be a resistive heater. The at least one second characteristic of the aerosol-generating device may comprise a temperature of the resistive heater. The electrical resistance of the resistive heater may be dependent on the temperature of the resistive heater. Depending on the composition of the resistive heater, as the resistive heater heats up, the electrical resistance may increase for example, resulting in a lower voltage drop across the internal resistance of the battery and thereby allowing for a greater duty cycle to be used.

The at least one second characteristic is different to the first characteristic of the battery. The at least one second characteristic may comprise a measure of battery age, such a count of charge and discharge cycles that the battery has completed. A count of charge and discharge cycles may be recorded and stored in a memory within the aerosol-generating device. Alternatively, the at least one second characteristic may comprise an internal resistance of the battery or an impedance of the battery. Alternatively, if the temperature of the battery is not used as the first characteristic of the battery, the temperature of the battery may be used as the at least one second characteristic.

The steps of measuring at least one second characteristic and selecting the value of duty cycle may be carried out periodically until the at least one second characteristic reaches a target value. In the example of a resistive heater, it may be desirable for the heater to reach a target temperature or target range of temperatures for production of a desired aerosol but not to exceed that target. When the target temperature is reached it is desirable to maintain the temperature rather than to maximise a duty cycle of the current supplied to the heater. A varying duty cycle can be used for the purpose of regulating the temperature of a heater. The higher the duty cycle, the higher the average current delivered by the battery to the heating element, and hence the higher the heating element temperature. Of course, reducing the duty cycle allows the contrary, e.g. to reduce the temperature of the heater.

The method may comprise monitoring a time since activation of the device, and if a target temperature is not reached within a predetermined time, deactivating or disabling the device.

The predetermined sub-rule may define a plurality of intervals of values related to the at least second characteristic of the aerosol-generating device, each interval being associated with a respective duty cycle value. The step of adjusting a value of the duty cycle using the control unit may comprise selecting the interval including the measured value of at least one second characteristic of the aerosol-generating device. The intervals of values related to the at least second characteristic of the aerosol-generating device may be sequential. The intervals of values related to the at least second characteristic of the aerosol-generating device may be non-overlapping.

For example, if the first characteristic of the battery is battery temperature and the second characteristic of the aerosol-generating device is heating element resistance, and the battery temperature is determined to be −2° C., which is in the second range in the example given above, then the sub-rule for that temperature range might be:

2.1/If the heating element resistance is between 0.8 and 1 ohm, use a duty cycle of 20%

2.2/If the heating element resistance is between 1 and 1.2 ohm, use a duty cycle of 30%

2.3/If the heating element resistance is between 1.2 and 1.4 ohm, use a duty cycle of 40%

2.4/If the heating element resistance is between 1.4 and 1.6 ohm, use a duty cycle of 50%

2.5/If the heating element resistance is between 1.6 and 1.8 ohm, use a duty cycle of 60%

2.6/If the heating element resistance is above 1.8 ohm, use any desired duty cycle.

For each interval of values related to the at least one characteristic of the battery in the predetermined rule there may be a different sub-rule.

The method may use further levels of sub-rules based on further measured characteristics. In particular, the method may comprise a step of measuring a third characteristic of the battery or aerosol-generating device and selecting the value of a duty cycle based on a predetermined sub-sub-rule and on the measured value of at least one third characteristic of the aerosol-generating device or battery, wherein the predetermined sub-sub-rule is selected from a group of predetermined sub-sub-rules based on a predetermined sub-rule, the measured second characteristic and the measured at least one first characteristic of the battery. For each interval of values of the second characteristic in a sub-rule there may be a group of sub-sub-rules specifying a duty cycle associated with different ranges of the third characteristic. Further levels of rules may be used in a hierarchy of rules based on a plurality of measured characteristics.

The method may further comprise periodically measuring an output battery voltage of the battery, calculating a rate of drop of output battery voltage based on measured output battery voltages, and reducing the duty cycle if the rate of drop of output battery voltage exceeds a threshold level. This is advantageous because it arrests or slows the fall in output battery voltage to a level at which it is still possible to ensure that that the control unit receives a minimum threshold voltage. For example, if, after a duty cycle of the current is increased in accordance with the predetermined rule, the rate of drop of output battery voltage is determined to be such that the output battery voltage would fall below a minimum operating voltage in only a few seconds, before the resistive heater could reach the target temperature, then the duty cycle could be reduced by 5%. There may be a different threshold level of rate of drop of output battery voltage for each interval within the predetermined rule or sub-rules. The rate of drop of output battery voltage may be periodically calculated more frequently than the first characteristic is measured. The rate of drop of output battery voltage may be periodically calculated more frequently than the second characteristic is measured.

The threshold level of rate of drop of output battery voltage may be set based on an initial output battery voltage. In one example the threshold level of rate of drop of output battery voltage could be defined by a minimum time it takes for the heater to increase its resistance to a particular value, such as 1.6 Ohm for 3.2V battery, therefore drawing 2 A of current. Then, the battery voltage should not drop below its minimum value (for example 2.5V) before this minimum time. The minimum time may be set as 5 seconds for example. If initial battery voltage value is 3.2V, then maximum rate of battery voltage drop would be: (3.2V–2.5V)/5=0.14 V/s. Alternatively, the threshold level of rate of drop of output battery voltage could be specified to a set value, independent of initial output battery voltage, say 0.5 V/s.

The method may further comprise subsequently increasing the duty cycle if the rate of drop of output battery voltage exceeds the threshold for a predetermined plurality of measurement cycles of output battery voltage.

The method may comprise deactivating or disabling the device if the duty cycle needs to be reduced below a minimum duty cycle.

In a second aspect, there is provided an aerosol-generating device, comprising:
   an aerosol-generating element;
   a control unit;
   a battery for delivering a current to the aerosol-generating element and to the control unit; and
   a measuring unit, connected to the control unit, for measuring at least one first characteristic of the battery;
   wherein the control unit is configured to adjust a duty cycle of the current delivered to the aerosol-generating element from the battery based on a predetermined rule which outputs a value of the duty cycle based on the at least one battery characteristic measured by the measuring unit.

The aerosol-generating device may comprise a non-volatile memory. The non-volatile memory may be part of the control unit. The non-volatile memory may store the predetermined rule.

The control unit may be configured to carry out a method in accordance with the first aspect of the invention. In particular, the control unit may be configured to use sub-rules as described in relation to the first aspect of the invention. The control unit may be configured to measure a rate of drop in output battery voltage as described in relation to the first aspect of the invention.

The control unit may comprise a switch. The control unit may be configured to adjust the duty cycle by operating the switch to turn the supply of current to the aerosol-generating element on and off. The switch may be a transistor, such as metal-oxide-semiconductor field-effect transistor (MOSFET).

The at least one characteristic of the battery may be battery temperature. The measuring unit may comprise a temperature sensor. Alternatively, the at least one battery characteristic may comprise a measure of battery age, such a count of charge and discharge cycles that the battery has completed. A count of charge and discharge cycles may be recorded and stored in an memory within the aerosol-generating device. Alternatively, the at least one battery characteristic may comprise an internal resistance of the battery or an impedance of the battery. The internal resistance and impedance of the battery may be measured using well known techniques, such as the method described in WO2014/029880

As used herein, an 'aerosol-generating device' relates to a device that interacts with an aerosol-forming substrate to generate an aerosol. The aerosol-forming substrate may be part of an aerosol-generating article. An aerosol-generating device may be a device that interacts with an aerosol-forming substrate of an aerosol-generating article to generate an aerosol that is directly inhalable into a user's lungs thorough the user's mouth. The aerosol generating element may be configured to heat, or otherwise atomise, an aerosol-forming substrate to form an aerosol. The aerosol-forming substrate may be fully or partially contained within the device.

The aerosol-forming substrate may be a solid aerosol-forming substrate. Alternatively, the aerosol-forming substrate may be a liquid or may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

Although reference is made to solid aerosol-forming substrates above, it will be clear to one of ordinary skill in the art that other forms of aerosol-forming substrate may be used with other embodiments. For example, the aerosol-forming substrate may be a liquid aerosol-forming substrate. If a liquid aerosol-forming substrate is provided, the aerosol-generating device preferably comprises means for retaining the liquid. For example, the liquid aerosol-forming substrate may be retained in a container. Alternatively or in addition, the liquid aerosol-forming substrate may be absorbed into a porous carrier material. The porous carrier material may be made from any suitable absorbent plug or body, for example, a foamed metal or plastics material, polypropylene, terylene, nylon fibres or ceramic. The liquid aerosol-forming substrate may be retained in the porous carrier material prior to use of the aerosol-generating device or alternatively, the liquid aerosol-forming substrate material may be released into the porous carrier material during, or immediately prior to use. For example, the liquid aerosol-forming substrate may be provided in a capsule. The shell of the capsule preferably melts upon heating and releases the liquid aerosol-forming substrate into the porous carrier material. The capsule may optionally contain a solid in combination with the liquid. Alternatively, the carrier may be a non-woven fabric or fibre bundle into which tobacco components have been incorporated. The non-woven fabric or fibre bundle may comprise, for example, carbon fibres, natural cellulose fibres, or cellulose derivative fibres.

During operation, the aerosol-forming substrate may be completely contained within the aerosol-generating device. In that case, a user may puff on a mouthpiece of the aerosol-generating device. Alternatively, during operation an aerosol-forming article containing the aerosol-forming substrate may be partially contained within the aerosol-generating device. In that case, the user may puff directly on the aerosol-forming article.

The aerosol-forming article may be substantially cylindrical in shape. The aerosol-forming article may be substantially elongate. The aerosol-forming article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The aerosol-forming article may have a total length between approximately 30 mm and approximately 100 mm. The aerosol-forming article may have an external diameter between approximately 5 mm and approximately 12 mm. The aerosol-forming article may comprise a filter plug. The filter plug may be located at the downstream end of the aerosol-forming article. The filter plug may be a cellulose acetate filter plug. The filter plug is approximately 7 mm in length in one embodiment, but may have a length of between approximately 5 mm to approximately 10 mm.

In one embodiment, the aerosol-forming article has a total length of approximately 45 mm. The aerosol-forming article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The aerosol-forming article may comprise an outer paper wrapper. Further, the aerosol-forming article may comprise a separation between the aerosol-forming substrate and the filter plug. The separation may be approximately 18 mm, but may be in the range of approximately 5 mm to approximately 25 mm.

The aerosol-generating element may be a resistive heater. The at least one second characteristic of the aerosol-generating element may be a temperature or an electrical resistance of the resistive heater.

The resistive heater may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum platinum, gold and silver. Examples of suitable metal alloys include stainless steel, nickel-, cobalt-, chromium-, aluminium- titanium- zirconium-, hafnium-, niobium-, molybdenum-, tantalum-, tungsten-, tin-, gallium-, manganese-, gold- and iron-containing alloys, and super-alloys based on nickel, iron, cobalt, stainless steel, Timetal® and iron-manganese-aluminium based alloys. In composite materials, the electrically resistive material may optionally be embedded in, encapsulated or coated with an insulating material or vice-versa, depending on the kinetics of energy transfer and the external physicochemical properties required.

The aerosol generating device may comprise an internal resistive heater or an external resistive heater, or both internal and external resistive heaters, where "internal" and "external" refer to the aerosol-forming substrate. An internal resistive heater may take any suitable form. For example, an internal resistive heater may take the form of a heating blade. Alternatively, the internal resistive heater may take the form of a casing or substrate having different electro-conductive portions, or an electrically resistive metallic tube. Alternatively, the internal resistive heater may be one or more heating needles or rods that run through the centre of the aerosol-forming substrate. Other alternatives include a heating wire or filament, for example a Ni—Cr (Nickel-Chromium), platinum, tungsten or alloy wire or a heating plate. Optionally, the internal resistive heater may be deposited in or on a rigid carrier material. In one such embodiment, the electrically resistive heater may be formed using a metal having a defined relationship between temperature and resistivity. In such an exemplary device, the metal may be formed as a track on a suitable insulating material, such as ceramic material, and then sandwiched in another insulating material, such as a glass. Heaters formed in this manner may be used to both heat and monitor the temperature of the heating elements during operation.

An external resistive heater may take any suitable form. For example, an external resistive heater may take the form of one or more flexible heating foils on a dielectric substrate, such as polyimide. The flexible heating foils can be shaped to conform to the perimeter of the substrate receiving cavity. Alternatively, an external heating element may take the form of a metallic grid or grids, a flexible printed circuit board, a moulded interconnect device (MID), ceramic heater, flexible carbon fibre heater or may be formed using a coating technique, such as plasma vapour deposition, on a suitable shaped substrate. An external resistive heater may also be formed using a metal having a defined relationship between temperature and resistivity. In such an exemplary device, the metal may be formed as a track between two layers of suitable insulating materials. An external resistive heater formed in this manner may be used to both heat and monitor the temperature of the external heating element during operation.

The resistive heater advantageously heats the aerosol-forming substrate by means of conduction. The heating element may be at least partially in contact with the substrate, or the carrier on which the substrate is deposited.

Alternatively, the heat from either an internal or external heater may be conducted to the substrate by means of a heat conductive element.

The battery may be a rechargeable battery. The battery may be a lithium ion battery, for example a Lithium-Cobalt, a Lithium-Iron-Phosphate, Lithium Titanate or a Lithium-Polymer battery. Alternatively, the battery may another form of rechargeable battery, such as a Nickel-metal hydride battery or a Nickel cadmium battery.

The measuring unit may be integral with the battery or may be located on or in a battery housing.

The control unit may comprise a microcontroller unit (MCU). The control unit may be programmable. The control unit may comprise a switch connected to the battery in series with the aerosol-generating element.

The device is preferably a portable or handheld device that is comfortable to hold between the fingers of a single hand. The device may be substantially cylindrical in shape and has a length of between 70 and 120 mm. The maximum diameter of the device is preferably between 10 and 20 mm. In one embodiment the device has a polygonal cross section and has a protruding button formed on one face. In this embodiment, the diameter of the device is between 12.7 and 13.65 mm taken from a flat face to an opposing flat face; between 13.4 and 14.2 taken from an edge to an opposing edge (i.e., from the intersection of two faces on one side of the device to a corresponding intersection on the other side), and between 14.2 and 15 mm taken from a top of the button to an opposing bottom flat face.

The aerosol-generating device may be an electrically heated aerosol-forming device.

In a third aspect of the invention, there is provided a computer program which, when run on programmable electric circuitry in a control unit of an electrically operated aerosol generating device, the aerosol-generating device comprising an aerosol-generating element, and a battery for delivering power to the aerosol-generating element and to the control unit, causes the programmable electric circuitry to perform a method according to the first aspect of the invention.

Although the disclosure has been described by reference to different aspects, it should be clear that features described in relation to one aspect of the disclosure may be applied to the other aspects of the disclosure.

Examples of the invention will now be described in detail with reference to the accompanying drawings, in which.

Figure 1:
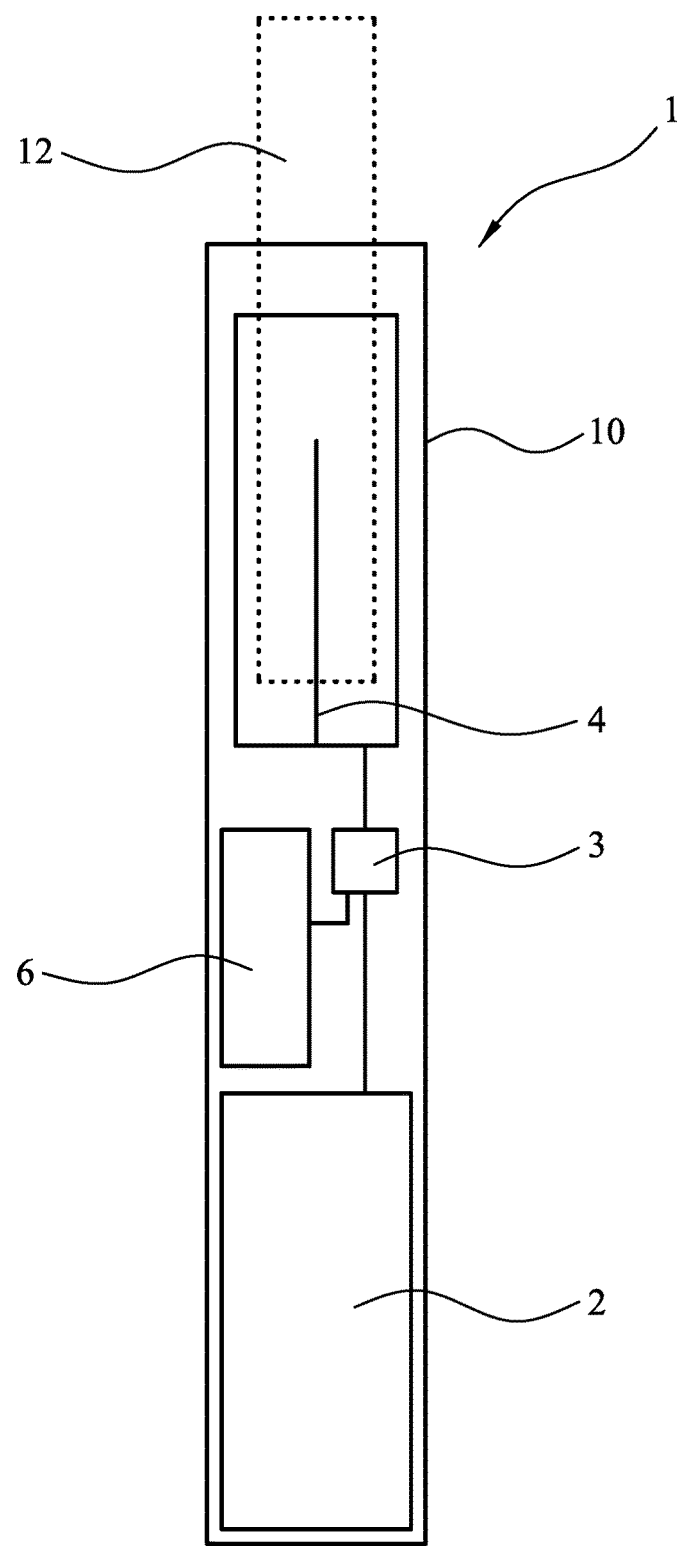
FIG. 1 is a schematic illustration of a device in accordance with an embodiment of the invention.

In FIG. 1, the components of an embodiment of an electrically heated aerosol generating device 1 are shown in a simplified manner. The elements of the electrically heated aerosol generating device 1 are not drawn to scale in FIG. 1. Elements that are not relevant for the understanding of this embodiment have been omitted to simplify FIG. 1.

The electrically heated aerosol generating device 1 comprises a housing 10 and an aerosol-forming substrate 12, for example a aerosol-forming article such as a cigarette. The aerosol-forming substrate 12 is pushed inside the housing 10 to come into thermal proximity with a heater 4. In this example, the heater is a blade that extends into the aerosol-forming substrate The aerosol-forming substrate 12 will release a range of volatile compounds at different temperatures. By controlling the maximum operation temperature of the heater to be below the release temperature of some of the volatile compounds, the release or formation of these smoke constituents can be avoided. Typically the aerosol-forming substrate is heated to a temperature of between 250 and 450 degrees centigrade. Within the housing 10 there is an electric battery 2, for example a rechargeable lithium ion battery. A control unit 3 is connected to the heating element 2, the electric battery 2, and a user interface 6, for example a button or display. This type of system is described in EP2800486 for example.

Figure 2:
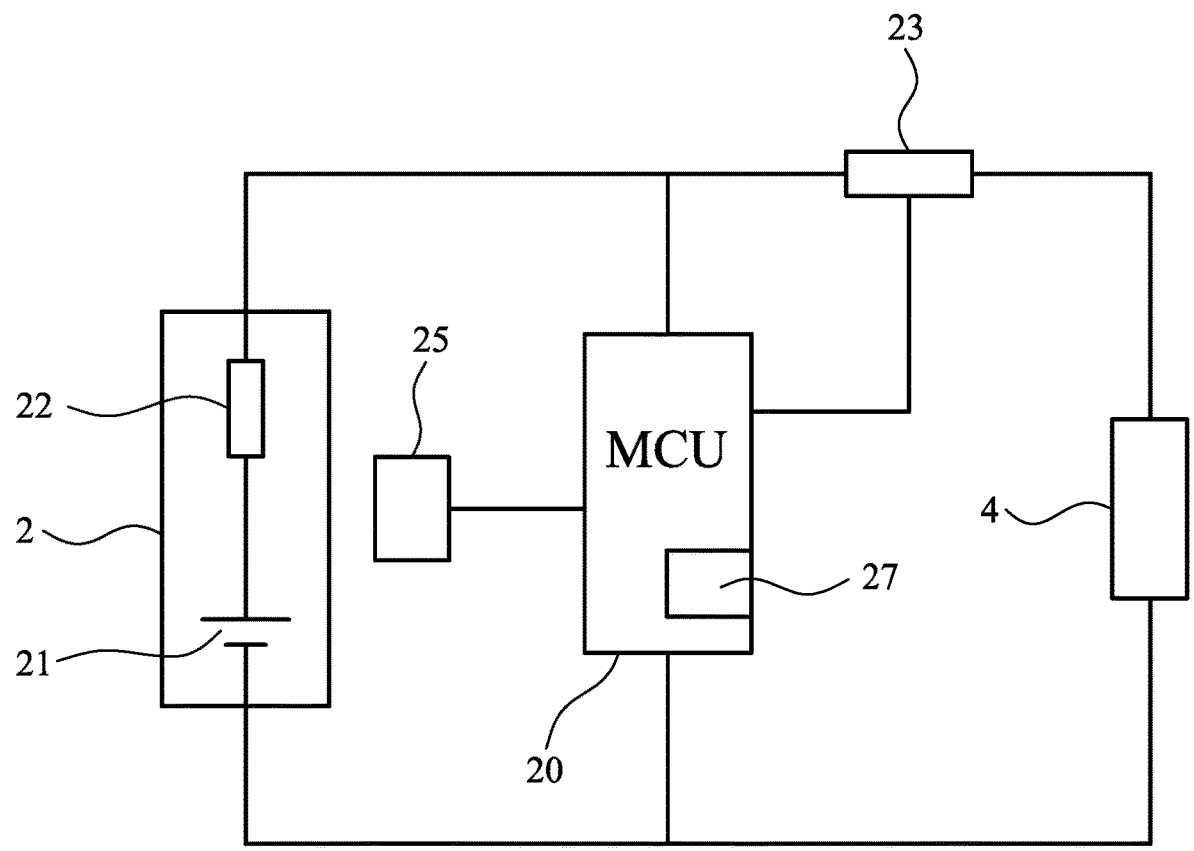
FIG. 2 illustrates the connection of the components of the device involved in a method in accordance with the invention.

The control unit 3 controls the power supplied to the heating element 4 in order to regulate its temperature by varying a duty cycle of the current. FIG. 2 illustrates the connection of battery, control unit and resistive heater in the device of FIG. 1.

The battery 2 is illustrated as an ideal battery 21 together with an internal resistance 22. The battery is connected to the resistive heater 4 through a control unit. The control unit comprises an microprocessor unit (MCU) 20 and a switch 23. The MCU controls the operation of the switch to control a duty cycle of the current delivered to the heater 4. The MCU 20 comprises a non-volatile memory 27.

The device also comprises a temperature sensor 25, positioned to measure a temperature of the battery 2. For example, the temperature sensor may be a thermistor to provide an analogue measurement of temperature, or a digital temperature sensor, such as LM75ADP from NXP. An output of the temperature sensor 25 is connected to the MCU 20. The temperature of the battery as measured by the temperature sensor 25 is used to control the operation of the switch 23 based on at least one rule stored in the non-volatile memory 27, as will be described.

The device may be activated by a user using the user interface 6. When the device is activated electrical current is delivered from the battery to the heater through the switch 23.

Ideally the heater is raised to a target temperature as quickly as possible after activation while ensuring that the MCU receives a sufficient voltage for proper function. At the outset, when the battery is cool, it will have a relatively high internal resistance, meaning that a greater proportion of the battery voltage will be dropped across the internal resistance that after the battery has heated up. This means that when the battery is cooler, a lower duty cycle for the current is desirable to ensure that the MCU receives at least a minimum operating voltage.

The voltage received by the MCU is also influenced by the resistance of the heater 4. The resistance of the heater 4 will typically vary during operation of the device, as it heats up. The heater may be formed from a material that has a significant variation of resistance with temperature so that the resistance of the heater can be used as a measure of the temperature of the heater for heater temperature control. The heater in this example has a positive temperature coefficient so that the resistance of the heater increases as the heater temperature increases.

The MCU may be configured to measure the electrical resistance of the heater 4. This may be achieved by using a shunt resistor (with a very low resistance) in series with the heater 4. The current through the shunt resistor, which is also the current through the heater, can be measured using an amplifier connected in parallel to the shunt resistor. The voltage across the heater can be measured directly and the resistance of the heater then calculated using Ohm's law. This is a well-known measurement technique.

Figure 3:
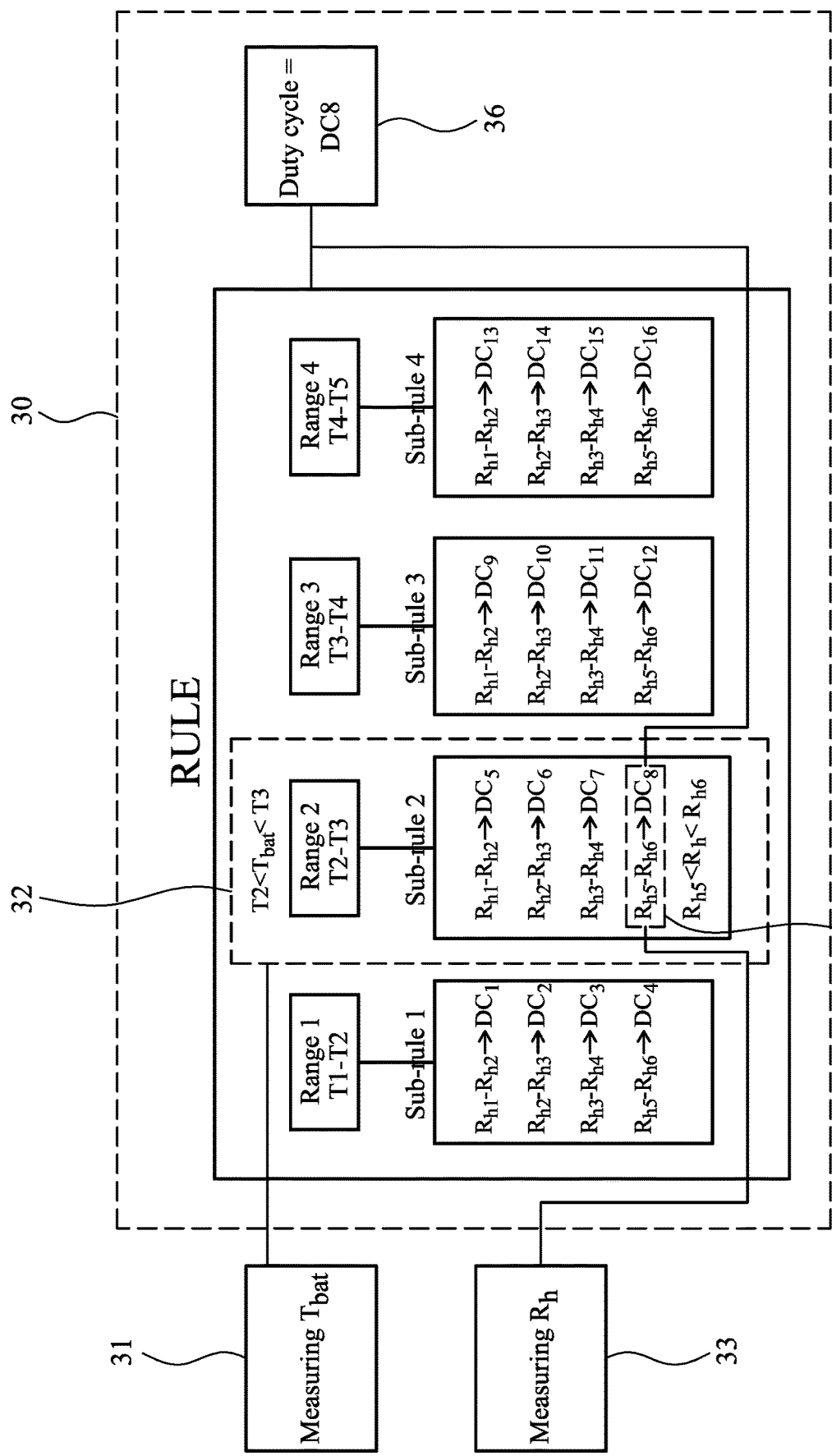
FIG. 3 illustrates a set of sub-rules in accordance with an embodiment of the invention.

The MCU controls the operation of the switch according to a rule stored in the memory of the MCU. FIG. 3 illustrates one example of a rule 30 that the MCU could use. The rule relates a measured temperature of the battery $T_{bat}$ and a measured electrical resistance of the heater $R_h$ to an output duty cycle. The rule comprises a plurality of sub-rules, each associated with a range of battery temperatures. The ranges of battery temperatures are sequential but do not overlap with each other. Within each sub-rule there is a plurality of duty cycles, each associated with a distinct range of heater resistances. The ranges of heater resistances are sequential but do not overlap with each other. To determine which duty cycle to use, the MCU first selects a sub-rule associated with a range of battery temperatures in which the measured battery temperature 31 falls. In the example illustrated in FIG. 3, this is Range 2, covering temperatures from T2 to T3, as illustrated by the dotted line box 32. The MCU then selects a duty cycle from within the sub-rule associated with Range 2. The duty cycle chosen is the duty cycle associated with the range of heater resistances in which the measured heater resistance 33 falls. In the example shown in FIG. 3, it is duty cycle DC8 associated with resistance range $R_{h5}$ to $R_{h6}$, as illustrated by the dotted line box 34. The output from the rule 30 is therefore DC8, as shown by box 36.

Instead of using heater resistance in the rule, another parameter, such as heater temperature could be used. The device may include a temperature sensor close to the heater. The output of the temperature sensor would be connected to the MCU.

The number of ranges and sub-ranges can be chosen according to particular design requirements and according to the construction of the heater 4. The example shown in FIG. 4 comprises four ranges of battery temperature and four ranges of heater resistance. In another embodiment, there are seven ranges of battery temperature as follows:

1/−10° C. to −5° C.
2/−5° C. to 0° C.
3/0° C. to 5° C.
4/5° C. to 10° C.
5/10° C. to 15° C.
6/15° C. to 20° C.
7/above 20° C.

And there are six ranges of heater resistance used in each sub-rule, as follows:

1/0.8 to 1 ohm
2/1 to 1.2 ohm
3/1.2 to 1.4 ohm
4/1.4 to 1.6 ohm
5/1.6 to 1.8 ohm
6/above 1.8 ohm.

The value of the duty cycle associated with each range in each sub-rule should be chosen to ensure that the MCU will always receive at least a minimum operating voltage required for proper function of the MCU. If the battery temperature is below −10° C. the device is disabled.

The process for adjusting the duty cycle of the current delivered to the heater is carried out periodically, for example every 0.5 seconds following activation of the device, until the heater reaches a target temperature or target resistance. So every 0.5 seconds a new sub-rule may be applied, depending on changes in the battery temperature and heater resistance.

If the heater does not reach a target temperature, for example 350° C., with a fixed time, for example 30 seconds, the heating process is stopped. In this situation, the battery cannot deliver enough power to the heater. This may be because the battery is old.

Figure 4:
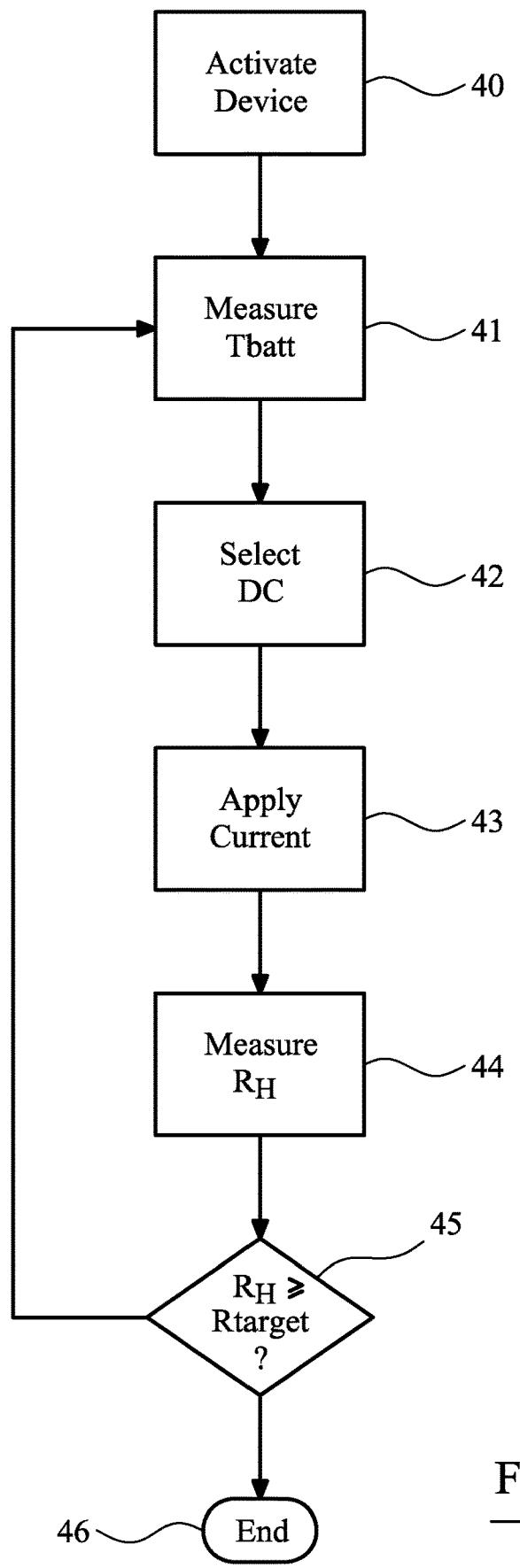
FIG. 4 is a flow diagram illustrating a control process according to an embodiment of the invention.

FIG. 4 is a flow chart showing an example control process using a rule of the type described above. The device is activated in step 40. In a first step 41 following activation the temperature of the battery is measured. Then, in step 42, a duty cycle for the current is selected based on the battery temperature. At this stage, before any current has been applied to the heater it is assumed that the heater resistance is at a maximum value. In step 43 the MCU operates the switch in accordance with the selected duty cycle to deliver current to the heater. This duty cycle is maintained for a predetermined period, such as 0.5 seconds. During this period the electrical resistance of the heater is measured, in step 44. In step 45 the measured electrical resistance is compared to a target resistance, corresponding to target heater temperature. If the heater resistance is equal to or greater than the target resistance then the process ends at step 46. If the heater resistance is less than the target resistance, indicating that the heater has not reached the target temperature, then the process returns to step 41 when the battery temperature is measured again. In step 42 the duty cycle is again selected using the predetermined rule, this time based on both battery temperature and heater resistance. The process is repeated until the target resistance is achieved or until 30 seconds after activation, whichever occurs sooner.

The benefit of the process described with reference to FIG. 4 is that it allows the maximum power to be extracted from the battery to heat the heater quickly, while keeping the battery voltage above a pre-defined threshold with a sufficient safety margin. The duty cycle is started at a low value and progressively raised as quickly as allowed, as the heater resistance rises and the battery temperature rises. This means that the heater is quickly but reliably heated to its target temperature.

Figure 5:
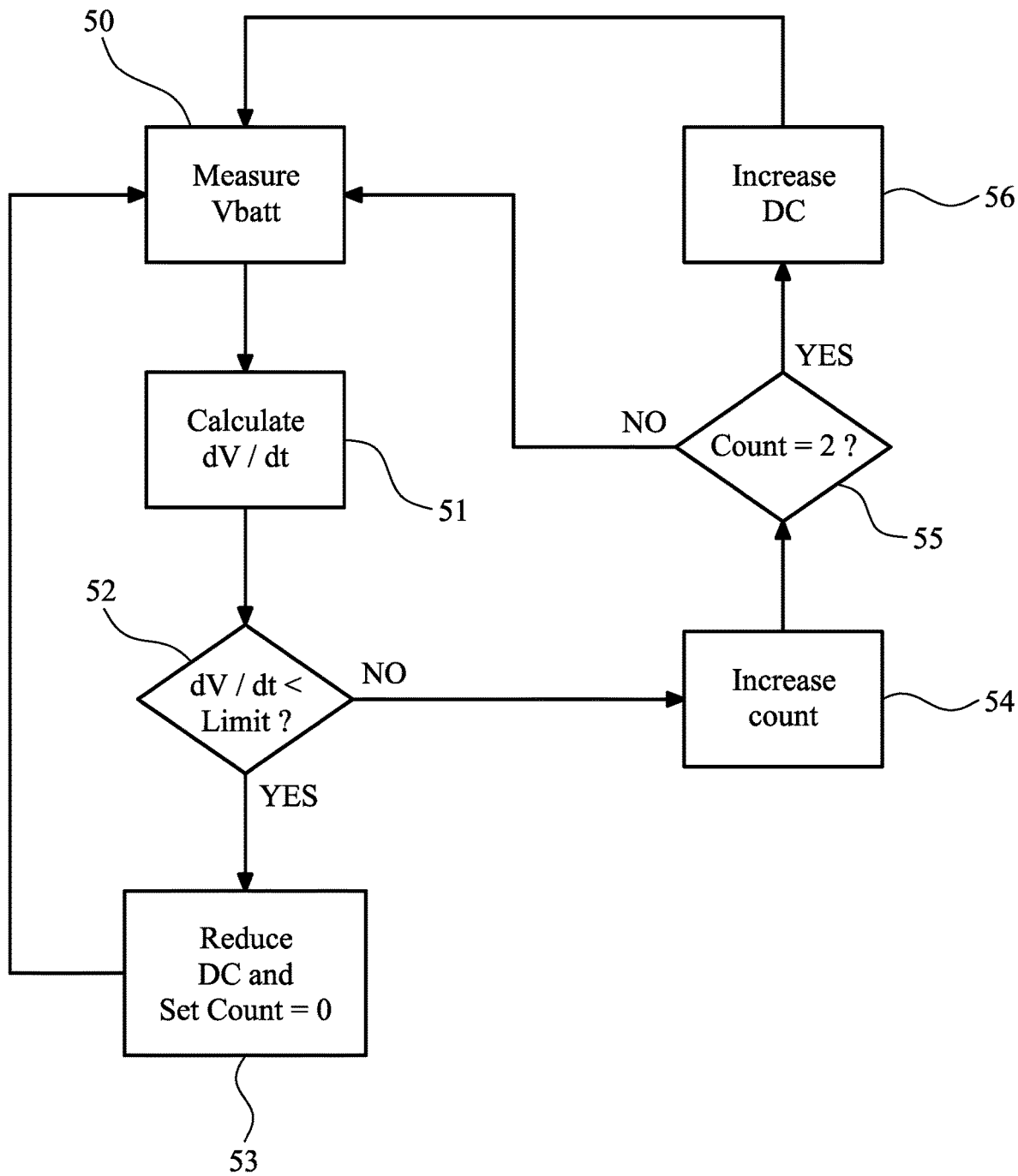
FIG. 5 is an additional control process used in an embodiment of the invention.

FIG. 5 illustrates an additional control process that may be used to further ensure that the MCU always receives a sufficient voltage during operation of the device.

For the process of FIG. 5, a maximum limit for the rate of output battery voltage drop is set, referred to here as the limit of rate of voltage drop. The limit of rate of voltage drop may be different for different sub-rules or different measured battery voltages.

If the rate of voltage drop is greater than the limit of rate of voltage drop, then the duty cycle of the current is reduced in order to slow the rate of voltage drop.

The process shown in FIG. 5 starts with step 50, in which the battery voltage is measured. In step 51 a rate of drop of battery voltage is calculated from the measured battery voltage and from measurements of battery voltage made in previous cycles of the process. In step 52 the MCU determines if the rate of drop of battery voltage is greater than the threshold (or if the rate of change of battery voltage is lower than the threshold). If the rate of drop of battery voltage is greater than the limit, then in step 53 the duty cycle is reduced by a predetermined amount. The process then returns to step 50. For example if the current duty cycle is 20% then a maximum rate of battery voltage drop of 0.5 V/s could be defined. The rate of battery voltage drop would be measured every 200 ms interval, for example. If, in step 52 the rate of drop of battery voltage is greater than the threshold, the duty cycle would be reduced from 20% to 15%, and then further reduced from 15% to 10% if rate of battery drop is still more than 0.5 V/s in the next cycle, after further 200 ms. A lower limit on the duty cycle of 5% could be set. If the process requires the duty cycle to be reduced from 5%, then the device may be deactivated.

This process is beneficial as it prevents the voltage at the MCU dropping below a minimum operational voltage as a result of a rapid voltage drop following a change in duty cycle. For example, if the output battery voltage starts at 3.4V, and the battery voltage drops at a rate of 0.5 V/s, a voltage of 2.4V would be reached in less than 2 seconds. This voltage is below the 2.5V minimum operating voltage and would be reached in only 2 seconds, which is not enough time to heat up the heater significantly.

The process of FIG. 5 also allows for duty cycle to be increased following a reduction if the rate of battery voltage drop increases. However the process requires the rate of voltage drop to be lower than the threshold for two cycles before the duty cycle is increased. To do this, a count is incremented for every cycle after an initial duty cycle drop in which the rate of drop of battery voltage is lower than the limit. If the rate of voltage drop is lower than the limit the count is incremented by one in step 54. If the rate of voltage drop is higher than the limit the count is reset to zero in step 53. Only if the count is determined to be equal to two in step 55 is the duty cycle increased in step 56. Otherwise the duty cycle is unchanged. In the example described, this means that the rate of drop of battery voltage must be less than 0.5 V/s for 400 ms, before going back up by step of 5% (instead of 200 ms when going down by step of 5%). This hysteresis provides stability to the system.

There may be other variables that affect the ideal duty cycle to use, such as the age of the battery (which may be measured as a count of the number of charge and discharge cycles it has performed), the internal resistance of the battery or the internal impedance of the battery. One or more of these variables may be used as the first or second characteristic. Alternatively, in order to provide finer control of duty cycle, it is possible to use a further tier or tiers of rules within the hierarchy of rules and sub-rules based on one or more of these variables. For example, a third characteristic may be a count of the charge and discharge cycles that the battery has been through. The count of charge and discharge cycles that the battery has been through may be recorded and stored in a memory within the control unit. Modifying the embodiment of FIG. 3, each sub-rule, based on heater resistance, instead of specifying a duty cycle to use for each measured heater resistance, may specify a plurality of sub-sub-rules to use for each value of heater resistance. Each sub-sub-rule may specify a duty cycle to use for a range of values for the count of charge and discharge cycles that the battery has been through. The sub-sub-rule used is selected based on the stored count of charge and discharge cycles in the memory of the control unit. In this way, the duty cycle is selected based on the temperature of the battery, the resistance of the heater and the number of charge and discharge cycles completed by the battery. The order in which the measured characteristics are assigned to the rules, sub-rules and sub-sub-rules may be varied.

The invention claimed is:

1. A method for controlling power supplied to an aerosol-generating element of an aerosol-generating device,
the aerosol-generating device comprising:
an aerosol-generating element,
a control unit, and
a battery configured to deliver power to the aerosol-generating element and to the control unit, the control unit being configured to adjust a duty cycle of a current supplied from the battery to the aerosol-generating element, the method comprising:
measuring, using a measuring unit, at least one first characteristic of the battery, the at least one first characteristic comprising a temperature of the battery; and
adjusting, using the control unit, a value of the duty cycle based on a predetermined rule which outputs the value of duty cycle based on the measured at least one battery characteristic.

2. The method according to claim 1, wherein the measuring and the adjusting are carried out periodically.

3. The method according to claim 1,
wherein the predetermined rule defines a plurality of intervals of values related to the at least one characteristic of the battery, each interval being associated with a respective duty cycle value, and
wherein the adjusting of the value of the duty cycle comprises outputting the duty cycle value associated with an interval including a value of the measured at least one battery characteristic.

4. The method according to claim 1,
further comprising measuring at least one second characteristic of the aerosol-generating device and selecting the value of duty cycle based on a predetermined sub-rule and on the measured value of the at least one second characteristic of the aerosol-generating device,
wherein the predetermined sub-rule is selected from a group of predetermined sub-rules based on the measured at least one first characteristic of the aerosol-generating device.

5. The method according to claim 4, wherein the measuring of the at least one second characteristic and the selecting the value of duty cycle are carried out periodically.

6. The method according to claim 4, wherein the measuring of the at least one second characteristic and the selecting the value of duty cycle are carried out periodically until the at least one second characteristic reaches a target value.

7. The method according to claim 4,
wherein the aerosol-generating element is a resistive heater, and
wherein the at least one second characteristic of the aerosol-generating device comprises a temperature of the resistive heater.

8. The method according to claim 4, wherein the at least one second characteristic of the aerosol-generating device comprises an electrical resistance of the aerosol-generating element.

9. The method according to claim 4, wherein the at least one second characteristic of the aerosol-generating device comprises a count of charge and discharge cycles that the battery has completed, and/or an internal resistance of the battery, and/or an impedance of the battery.

10. The method according to claim 5,
wherein the predetermined sub-rule defines a plurality of intervals of values related to the at least second characteristic of the aerosol-generating device, each interval of the plurality being associated with a respective duty cycle value, and
wherein the adjusting, using the control unit, of the value of the duty cycle comprises selecting an interval of the plurality including the measured value of the at least one second characteristic of the aerosol-generating device.

11. The method according to claim 1, further comprising periodically measuring an output battery voltage of the battery and calculating a rate of drop of output battery voltage based on measured output battery voltages, and reducing the duty cycle if a rate of drop of output battery voltage exceeds a threshold level.

12. The method according to claim 11, further comprising subsequently increasing the duty cycle if the rate of drop of output battery voltage exceeds the threshold level for a predetermined plurality of measurement cycles of output battery voltage.

13. An aerosol-generating device, comprising:
an aerosol-generating element;
a control unit;
a battery configured to deliver a current to the aerosol-generating element and to the control unit; and
a measuring unit configured to measure at least one first characteristic of the battery,
wherein the at least one first characteristic comprises a temperature of the battery, and
wherein the control unit is configured to adjust a duty cycle of a current delivered to the aerosol-generating element from the battery based on a predetermined rule which outputs a value of the duty cycle based on the at least one battery characteristic measured by the measuring unit.

14. The aerosol-generating device according to claim 13, wherein the aerosol-generating element is an electrically resistive heater.

15. The aerosol-generating device according to claim 13, wherein the battery is a lithium ion battery.

* * * * *